US007993885B2

(12) United States Patent
Gunji et al.

(10) Patent No.: US 7,993,885 B2
(45) Date of Patent: *Aug. 9, 2011

(54) METHOD FOR PRODUCING L-LYSINE OR L-ARGININE BY USING METHANOL ASSIMILATING BACTERIUM

(75) Inventors: Yoshiya Gunji, Kawasaki (JP); Hisashi Yasueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 412 days.

This patent is subject to a terminal disclaimer.

(21) Appl. No.: 11/563,289

(22) Filed: Nov. 27, 2006

(65) Prior Publication Data

US 2008/0199919 A1 Aug. 21, 2008

Related U.S. Application Data

(63) Continuation of application No. 10/166,142, filed on Jun. 11, 2002, now Pat. No. 7,169,587.

(30) Foreign Application Priority Data

Jun. 12, 2001 (JP) ................................. 2001-177075

(51) Int. Cl.
*C12P 13/08* (2006.01)
*C12N 1/20* (2006.01)
*C12N 15/00* (2006.01)
*C07K 1/00* (2006.01)
*C07H 21/02* (2006.01)

(52) U.S. Cl. ................ 435/115; 435/252.3; 435/252.33; 435/320.1; 530/350; 536/23.1

(58) Field of Classification Search .................. None
See application file for complete search history.

(56) References Cited

U.S. PATENT DOCUMENTS

| 5,643,758 | A | 7/1997 | Guan et al. |
|---|---|---|---|
| 5,972,663 | A | 10/1999 | Winterhalter et al. |
| 6,303,381 | B1 | 10/2001 | Gunji et al. |
| 6,878,533 | B2 | 4/2005 | Tsujimoto et al. |
| 6,911,332 | B2 | 6/2005 | Usuda et al. |
| 7,026,149 | B2 | 4/2006 | Usuda et al. |
| 7,029,893 | B2 | 4/2006 | Usuda et al. |
| 7,060,475 | B2 | 6/2006 | Usuda et al. |
| 7,169,587 | B2 * | 1/2007 | Gunji et al. .................. 435/115 |
| 2003/0113899 | A1 | 6/2003 | Yamaguchi et al. |
| 2003/0124687 | A1 | 7/2003 | Gunji et al. |
| 2003/0166174 | A1 | 9/2003 | Ono et al. |
| 2004/0142435 | A1 | 7/2004 | Gunji et al. |
| 2004/0146974 | A1 | 7/2004 | Gunji et al. |
| 2004/0166570 | A1 | 8/2004 | Asahara et al. |
| 2004/0171134 | A1 | 9/2004 | Asahara et al. |
| 2004/0191875 | A1 | 9/2004 | Takeshita et al. |
| 2004/0214296 | A1 | 10/2004 | Asahara et al. |
| 2004/0229311 | A1 | 11/2004 | Hirano et al. |
| 2005/0003495 | A1 | 1/2005 | Gunji et al. |
| 2005/0176121 | A1 | 8/2005 | Takeshita et al. |
| 2005/0208634 | A1 | 9/2005 | Usuda et al. |
| 2005/0233416 | A1 | 10/2005 | Tsujimoto et al. |
| 2006/0019355 | A1 | 1/2006 | Ueda et al. |
| 2006/0019356 | A1 | 1/2006 | Usuda et al. |
| 2006/0030010 | A1 | 2/2006 | Usuda et al. |
| 2006/0030011 | A1 | 2/2006 | Usuda et al. |
| 2006/0035347 | A1 | 2/2006 | Usuda et al. |
| 2006/0040365 | A1 | 2/2006 | Kozlov et al. |

FOREIGN PATENT DOCUMENTS

| AU | 724536 | | 7/1997 |
|---|---|---|---|
| EP | 1016710 | | 7/2000 |
| EP | 1188822 | * | 3/2002 |
| WO | WO97/23597 | | 7/1997 |
| WO | WO 00/61723 | * | 10/2000 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Gunji et al. J Biotechnol. Dec. 15, 2006;127(1):1-13. Epub Jun. 15, 2006.*
Accession X96471. Mar. 19, 2001.
Attwood, T. K., et al., "Which craft is best in bioinformaties?" Comp. and Chem. 2001;25:329-339.
Balbás, P., et al., "A pBRINT family of plasmids for integration of cloned DNA into the *Escherichia coli* chromosome," Gene 1996;172:65-69.
Bellmann, A., et al., "Expression control and specificity of the basic amino acid exporter LysE of *Corynebacterium glutamicum*," Microbiol. 2001;157:1765-1774.
European Search Report for EP App. No. 02012539.9 (Dec. 3, 2003).
Lee, G. H., et al., "Lysine Production from Methanol at 50°C. Using *Bacillus methanolicus*: Modeling Volume Control, Lysine Concentration, and Productivity Using a Three-Phase Continuous Simulation," Biotech. Bioengin. 1996;49:639-653.
Motoyama, H., et al, "Amino Acid Production from Methano by *Methylobacillus glycogens* Mutants; Isolation of L-Glutamic Acid Hyper-producing Mutants from *M. glycogens* Strains, and Derivation of L-Threonine and L-Lysine-producing Mutants from Them," Biosci. Biotech. Biochem. 1993;57(1):82-87.
Motoyama, H., et al., "Characterization of the Aspartate Family Amino Acids Biosynthetic Enzymes in L-Threonine and L-Lysine-producing Mutants of *Methylobacillus glycogens*," Biosci. Biotech. Biochem. 1993;57(3):461-466.
Motoyama, H., et al., "Overproduction of L-Lysine from Methanol by *Methlobacillus glycogens* Derivatives Carrying a Plasmid with a Mutated dapA Gene," Appl. Environmen. Microbiol. 2001;67(7)3064-3070.
Ponting, C. P. "Issues in predicting protein function from sequence," Brief. Bioinform. 2001;2(1):19-29.

(Continued)

Primary Examiner — Christian Fronda
(74) Attorney, Agent, or Firm — Shelly Guest Cermak; Cermak Nakajima LLP

(57) ABSTRACT

A DNA encoding a variant of a protein having a loop region and six hydrophobic helixes which is involved in excretion of L-lysine to outside of a cell is described, wherein the DNA encodes a mutant protein which does not contain the loop region that is present in the wild-type protein. The mutant protein facilitates excretion of L-lysine, L-arginine, or both to the outside of the cell of a methanol assimilating bacterium when the DNA is introduced into the bacterium. Specifically, lysE24 is introduced into a methanol assimilating bacterium such as *Methylophilus* bacteria which results in improved L-amino acid productivity, especially production of L-lysine and L-arginine.

4 Claims, 2 Drawing Sheets

OTHER PUBLICATIONS

Presentation slides and speech by Yoshiya Gunhji at the Annual Meeting of the Society for Biotechnology, Japan held at Meijyou University on Sep. 23, 2004.

Roche, B., et al., "A *Bacillus subtilis* chromosome segment at the 100° to 102° position encoding 11 membrane proteins," Microbiol. 1997;143:3309-3312.

Schendel, F. J., et al., "L-Lysine Production at 50°C. by Mutants of a Newly Isolated and Characterized Methylotrophic *Bacillus* sp." Appl. Environmen. Microbiol. 1990;56(4):963-970.

Vrljic, M., et al., "A new type of transporter with a new type of cellular function: L-lysine export from *Corynebacterium glutamicum*," Mol. Microbiol. 1996;22(5):815-826.

Vrljic, M., et al., "The LysE Superfamily: Topology of the Lysine Exporter LysE of *Corynebacterium glutamicum*, a Paradyme for a Novel Superfamily of Transmembrane Solute Translocators," J. Mol. Microbiol. Biotechnol. 1999;1(2):327-336.

* cited by examiner

SEQUENCE LISTING

```
<160> NUMBER OF SEQ ID NOS: 10

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 1
agggaattcc ccgttctgga taatgttttt tgcgccgac                    39

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence: primer

<400> SEQUENCE: 2
cggatgcatc tagagttaac ctgcagggtg aaattgttat ccgctcacaa ttccacac    58

<210> SEQ ID NO 3
<211> LENGTH: 35
<212> TYPE: DNA
<213> ORGANISM: Artificial Sequence
```

```
<220> FEATURE:
<223> OTHER INFORMATION: Description of Artificial Sequence: primer

<400> SEQUENCE: 3
tgacctgcag gtttgcacag aggatggccc atgtt                               35

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 4
cattctagat ccctaaactt tacagcaaac cggcat                              36

<210> SEQ ID NO 5
<211> LENGTH: 64
<212> TYPE: DNA
<213> ORGANISM: Artificial Sequence
<220> FEATURE:
<223> OTHER INFORMATION: Description of Artificial Sequence: primer

<400> SEQUENCE: 5
catttcctgc aggcaaagga gatgagcgta atggtgatca tggaaatctt cattacaggt    60
ctgc                                                                 64

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 6
gggcgagcta gaagagctcc aaaacccgcg aaaactaacc catcaacatc               50

<210> SEQ ID NO 7
<211> LENGTH: 711
<212> TYPE: DNA
<213> ORGANISM: Brevibacterium lactofermentum
<220> FEATURE:
<221> NAME/KEY: CDS
<222> LOCATION: (1)..(711)

<400> SEQUENCE: 7 atg gtg atc atg gaa atc ttc att aca ggt ctg ctt ttg ggg gcc agt      48
Met Val Ile Met Glu Ile Phe Ile Thr Gly Leu Leu Leu Gly Ala Ser
 1               5                  10                  15 ctt tta ctg tcc atc gga ccg cag aat gta ctg gtg att aaa caa gga      96
Leu Leu Leu Ser Ile Gly Pro Gln Asn Val Leu Val Ile Lys Gln Gly
            20                  25                  30 att aag cgc gaa gga ctc att gcg gtt ctt ctc gtg tgt tta att tct     144
Ile Lys Arg Glu Gly Leu Ile Ala Val Leu Leu Val Cys Leu Ile Ser
        35                  40                  45 gac gtc ttt ttg ttc atc gcc ggc acc ttg ggc gtt gat ctt ttg tcc     192
Asp Val Phe Leu Phe Ile Ala Gly Thr Leu Gly Val Asp Leu Leu Ser
    50                  55                  60 aat gcc gcg ccg atc gtg ctc gat att atg cgc tgg ggt ggc atc gct     240
Asn Ala Ala Pro Ile Val Leu Asp Ile Met Arg Trp Gly Gly Ile Ala
65                  70                  75                  80 tac ctg tta tgg ttt gcc gtc atg gca gcg aaa gac gcc atg aca aac     288
Tyr Leu Leu Trp Phe Ala Val Met Ala Ala Lys Asp Ala Met Thr Asn
                85                  90                  95
```

```
aag gtg gaa gcg cca cag atc att gaa gaa aca gaa cca acc gtg ccc          336
Lys Val Glu Ala Pro Gln Ile Ile Glu Glu Thr Glu Pro Thr Val Pro
            100                 105                 110 gat gac acg cct ttg ggc ggt tcg gcg gtg gcc act gac acg cgc aac          384
Asp Asp Thr Pro Leu Gly Gly Ser Ala Val Ala Thr Asp Thr Arg Asn
        115                 120                 125 cgg gtg cgg gtg gag gtg agc gtc gat aag cag cgg gtt tgg gta aag          432
Arg Val Arg Val Glu Val Ser Val Asp Lys Gln Arg Val Trp Val Lys
    130                 135                 140 ccc atg ttg atg gca atc gtg ctg acc tgg ttg aac ccg aat gcg tat          480
Pro Met Leu Met Ala Ile Val Leu Thr Trp Leu Asn Pro Asn Ala Tyr
145                 150                 155                 160 ttg gac gcg ttt gtg ttt atc ggc ggc gtc ggc gcg caa tac ggc gac          528
Leu Asp Ala Phe Val Phe Ile Gly Gly Val Gly Ala Gln Tyr Gly Asp
                165                 170                 175 acc gga cgg tgg att ttc gcc gct ggc gcg ttc gcg gca agc ctg atc          576
Thr Gly Arg Trp Ile Phe Ala Ala Gly Ala Phe Ala Ala Ser Leu Ile
            180                 185                 190 tgg ttc ccg ctg gtg ggt ttc ggc gca gca gca ttg tca cgc ccg ctg          624
Trp Phe Pro Leu Val Gly Phe Gly Ala Ala Ala Leu Ser Arg Pro Leu
        195                 200                 205 tcc agc ccc aag gtg tgg cgc tgg atc aac gtc gtc gtg gca gtt gtg          672
Ser Ser Pro Lys Val Trp Arg Trp Ile Asn Val Val Val Ala Val Val
    210                 215                 220 atg acc gca ttg gcc atc aaa ctg atg ttg atg ggt tag                      711
Met Thr Ala Leu Ala Ile Lys Leu Met Leu Met Gly
225                 230                 235

<210> SEQ ID NO 8
<211> LENGTH: 236
<212> TYPE: PRT
<213> ORGANISM: Brevibacterium lactofermentum

<400> SEQUENCE: 8

Met Val Ile Met Glu Ile Phe Ile Thr Gly Leu Leu Leu Gly Ala Ser
1               5                   10                  15

Leu Leu Leu Ser Ile Gly Pro Gln Asn Val Leu Val Ile Lys Gln Gly
            20                  25                  30

Ile Lys Arg Glu Gly Leu Ile Ala Val Leu Leu Val Cys Leu Ile Ser
        35                  40                  45

Asp Val Phe Leu Phe Ile Ala Gly Thr Leu Gly Val Asp Leu Leu Ser
    50                  55                  60

Asn Ala Ala Pro Ile Val Leu Asp Ile Met Arg Trp Gly Gly Ile Ala
65                  70                  75                  80

Tyr Leu Leu Trp Phe Ala Val Met Ala Ala Lys Asp Ala Met Thr Asn
                85                  90                  95

Lys Val Glu Ala Pro Gln Ile Ile Glu Glu Thr Glu Pro Thr Val Pro
            100                 105                 110

Asp Asp Thr Pro Leu Gly Gly Ser Ala Val Ala Thr Asp Thr Arg Asn
        115                 120                 125

Arg Val Arg Val Glu Val Ser Val Asp Lys Gln Arg Val Trp Val Lys
    130                 135                 140

Pro Met Leu Met Ala Ile Val Leu Thr Trp Leu Asn Pro Asn Ala Tyr
145                 150                 155                 160

Leu Asp Ala Phe Val Phe Ile Gly Gly Val Gly Ala Gln Tyr Gly Asp
                165                 170                 175

Thr Gly Arg Trp Ile Phe Ala Ala Gly Ala Phe Ala Ala Ser Leu Ile
            180                 185                 190
```

```
Trp Phe Pro Leu Val Gly Phe Gly Ala Ala Ala Leu Ser Arg Pro Leu
        195                 200                 205

Ser Ser Pro Lys Val Trp Arg Trp Ile Asn Val Val Ala Val Val
    210                 215                 220

Met Thr Ala Leu Ala Ile Lys Leu Met Leu Met Gly
225                 230                 235

<210> SEQ ID NO 9
<211> LENGTH: 712
<212> TYPE: DNA
<213> ORGANISM: Brevibacterium lactofermentum
<220> FEATURE:
<221> NAME/KEY: CDS
<222> LOCATION: (1)..(375)

<400> SEQUENCE: 9 atg gtg atc atg gaa atc ttc att aca ggt ctg ctt ttg ggg gcc agt     48
Met Val Ile Met Glu Ile Phe Ile Thr Gly Leu Leu Leu Gly Ala Ser
  1               5                  10                  15 ctt ttg ctg tcc atc gga ccg cag aat gta ctg gtg att aaa caa gga     96
Leu Leu Leu Ser Ile Gly Pro Gln Asn Val Leu Val Ile Lys Gln Gly
             20                  25                  30 att aag cgc gaa gga ctc att gcg gtt ctt ctc gtg tgt tta att tct    144
Ile Lys Arg Glu Gly Leu Ile Ala Val Leu Leu Val Cys Leu Ile Ser
         35                  40                  45 gac gtc ttt ttg ttc atc gcc ggc acc ttg ggc gtt gat ctt ttg tcc    192
Asp Val Phe Leu Phe Ile Ala Gly Thr Leu Gly Val Asp Leu Leu Ser
     50                  55                  60 aat gcc gcg ccg atc gtg ctc gat att atg cgc tgg ggt ggc atc gct    240
Asn Ala Ala Pro Ile Val Leu Asp Ile Met Arg Trp Gly Gly Ile Ala
 65                  70                  75                  80 tac ctg tta tgg ttt gcc gtc atg gca gcg aaa gac gcc atg aca aac    288
Tyr Leu Leu Trp Phe Ala Val Met Ala Ala Lys Asp Ala Met Thr Asn
                 85                  90                  95 aag gtg gaa gcg cca cag atc att gaa gaa aca gaa cca acc gtg ccc    336
Lys Val Glu Ala Pro Gln Ile Ile Glu Glu Thr Glu Pro Thr Val Pro
            100                 105                 110 gat gac acg cct ttg ggc gtg ttc ggc ggt ggc cac tga cacgcgcaac    385
Asp Asp Thr Pro Leu Gly Val Phe Gly Gly Gly His
            115                 120 cgggtgcggg tggaggtgag cgtcgataag cagcgggttt gggtgaagcc catgttgatg    445
gcaatcgtgc tgacctggtt gaacccgaat gcgtatttgg acgcgtttgt gtttatcggc    505
ggcgtcggcg cgcaatacgg cgacaccgga cggtggattt tcgccgctgg cgcgttcgcg    565
gcaagcctga tctggttccc gctggtgggt ttcggcgcag cagcattgtc acgcccgctg    625
tccagcccca aggtgtggcg ctggatcaac gtcgtcgtgg cagttgtgat gaccgcattg    685
gccatcaaac tgatgttgat gggttag                                      712

<210> SEQ ID NO 10
<211> LENGTH: 124
<212> TYPE: PRT
<213> ORGANISM: Brevibacterium lactofermentum

<400> SEQUENCE: 10

Met Val Ile Met Glu Ile Phe Ile Thr Gly Leu Leu Leu Gly Ala Ser
  1               5                  10                  15

Leu Leu Leu Ser Ile Gly Pro Gln Asn Val Leu Val Ile Lys Gln Gly
             20                  25                  30

Ile Lys Arg Glu Gly Leu Ile Ala Val Leu Leu Val Cys Leu Ile Ser
         35                  40                  45
```

```
-continued

Asp Val Phe Leu Phe Ile Ala Gly Thr Leu Gly Val Asp Leu Leu Ser
     50                  55                  60

Asn Ala Ala Pro Ile Val Leu Asp Ile Met Arg Trp Gly Gly Ile Ala
 65              70                  75                      80

Tyr Leu Leu Trp Phe Ala Val Met Ala Ala Lys Asp Ala Met Thr Asn
             85                  90                  95

Lys Val Glu Ala Pro Gln Ile Ile Glu Glu Thr Glu Pro Thr Val Pro
            100                 105                 110

Asp Asp Thr Pro Leu Gly Val Phe Gly Gly Gly His
            115             120
```

METHOD FOR PRODUCING L-LYSINE OR L-ARGININE BY USING METHANOL ASSIMILATING BACTERIUM

This application claims priority as a continuation under 35 U.S.C. §120 to U.S. application Ser. No. 10/166,142, filed Jun. 11, 2002 now U.S. Pat. No. 7,169,587, the entirety of which is incorporated by reference.

BACKGROUND OF THE INVENTION

1. Field of the Invention

The present invention relates to techniques used in the field of microbial industry. More precisely, the present invention relates to a method for producing L-lysine or L-arginine by fermentation and a microorganism used in the production method.

2. Brief Description of the Background Art

Amino acids such as L-lysine, L-glutamic acid, L-threonine, L-leucine, L-isoleucine, L-valine and L-phenylalanine are industrially produced by fermentation using microorganisms such as those that belong to the genus *Brevibacterium, Corynebacterium, Bacillus, Escherichia, Streptomyces, Pseudomonas, Arthrobacter, Serratia, Penicillium, Candida*, or the like. In order to improve the productivity of these microorganisms, strains isolated from nature or artificial mutants thereof have been used. Moreover, various techniques have been disclosed for increasing the L-amino acid producing abilities by using recombinant DNA techniques to enhance L-amino acid biosynthetic enzymes.

Production of L-amino acids has been improved considerably by breeding microorganisms such as those mentioned above, and improving various production methods. However, in order to respond to further increase in demand in the future, development of methods for more efficient production of L-amino acids at a lower cost are still desirable.

Methods for producing L-amino acids by fermentation of methanol, which is a fermentation raw material available in large amounts at a low cost, include known methods using microorganisms that belong to the genus *Achromobacter* or *Pseudomonas* (Japanese Patent Laid-open (Kokai) No. 45-25273), *Protaminobacter* (Japanese Patent Publication (Kokoku) No. 49-125590), *Protaminobacter* or *Methanomonas* (Japanese Patent Laid-open No. 50-25790), *Microcyclus* (Japanese Patent Laid-open No. 52-18886), *Methylobacillus* (Japanese Patent Laid-open No. 4-91793), *Bacillus* (Japanese Patent Laid-open No. 3-505284) and so forth. The inventors of the present invention have developed methods for producing L-amino acids using *Methylophilus* bacteria based on breeding by artificial mutagenesis and recombinant DNA techniques (Japanese Patent Application No. 11-368097).

In recent years, proteins have been identified that specifically secrete an L-amino acid to the outside of a cell, as well as the genes therefor. In particular, Vrljic et al. identified a gene which is involved in the secretion of L-lysine from a *Corynebacterium* bacterium to outside of a cell (Vrljic M., Sahm H., Eggeling L., Molecular Microbiology 22:815-826 (1996)). This gene was designated lysE, and it was reported that the L-lysine producing ability of *Corynebacterium* bacteria could be improved by enhancing this gene in *Corynebacterium* bacteria (WO97/23597). It is also known that production of some L-amino acids can be improved by increasing the expression of amino acid excreting proteins in *Escherichia coli* (Japanese Patent Laid-open No. 2000-189180). For example, it has been reported that production of cysteine, cysteine, and so forth can be improved by enhancing expression of ORF306 gene in *Escherichia coli* (EP885962).

However, there has been disclosed no indication that the amino acid excretion process constitutes a serious obstacle for amino acid production by fermentation of methanol in methanol assimilating bacteria. Furthermore, there have been no reports as to any amino acid excretion gene that can provide such a secretion activity in a methanol assimilating bacterium.

Furthermore, it has not been previously reported that the lysE gene has a function of excreting amino acids other than L-lysine.

SUMMARY OF THE INVENTION

An object of the present invention is to provide a method for efficiently producing L-lysine or L-arginine by using methanol, which is available in large amounts at a low cost.

The inventors of the present invention assiduously studied in order to achieve the aforementioned object. As a result, they found that, when an L-amino acid is produced by utilizing a methanol assimilating bacterium, especially a *Methylophilus* bacterium, there were barriers in the excretion process of the L-amino acid to the outside of cell. Furthermore, they successfully isolated a gene that could provide excretion activity of the amino acids, especially in the microorganism, and overcome the barriers in the excretion process. Therefore, it was determined that the use of this gene enabled efficient amino acid production.

The inventors of the present invention introduced the already known lysE gene derived from a *Corynebacterium* bacterium into a methanol assimilating bacterium and investigated its effect on amino acid production. However, a mutation or deletion was introduced into the lysE gene, and thus lysE failed to function. Since the protein responsible for such excretion exerts its function when it is incorporated into a cytoplasmic membrane, there must be suitable relationships between the protein and properties of the membrane, such as its lipid composition. Therefore, it is considered difficult to obtain expression of a membrane protein of heterogenous origin in a form that exerts its function, and the above results supported this finding.

The inventors of the present invention obtained a mutant gene that could function in a methanol assimilating bacterium during study of the aforementioned genes for excretion of L-amino acids. They also found a remarkable effect of the utilization of the mutant gene in amino acid production using a methanol assimilating bacterium.

The present invention was accomplished as described above and provides the following.

It is an object of the present invention to provide a DNA encoding a variant protein, wherein said wild-type protein has a loop region and six hydrophobic helixes, and is involved in excretion of L-lysine to outside of a cell, and wherein the variant protein does not contain said loop region and wherein said variant protein facilitates excretion of L-lysine, L-arginine or both to the outside of a methanol assimilating bacterium when the DNA is introduced into the bacterium.

It is an object of the present invention to provide the DNA as described above, wherein the variant protein consists of substantially only the hydrophobic helixes.

It is an object of the present invention to provide the DNA as described above, wherein the variant protein has all of the six hydrophobic helixes.

It is an object of the present invention to provide the DNA as described above, which encodes a peptide containing the first to third hydrophobic helixes from the N-terminus and a peptide containing the fourth to sixth hydrophobic helixes from the N-terminus.

It is an object of the present invention to provide the DNA as described above, wherein the protein is LysE protein.

It is an object of the present invention to provide the DNA as described above, wherein the LysE protein is from coryneform bacterium.

It is an object of the present invention to provide the DNA as described above, wherein the methanol assimilating bacterium is a *Methylophilus* bacterium.

It is an object of the present invention to provide a DNA encoding a protein selected from the group consisting of:

(A) a protein which comprises the amino acid sequence of SEQ ID NO: 10, and (B) a protein which comprises the amino acid sequence consisting of the amino acid sequence of SEQ ID NO: 10 including substitution, deletion, insertion or addition of one or several amino acid residues and has an activity for facilitating excretion of L-lysine, L-arginine or both to the outside of a methanol assimilating bacterium.

It is an object of the present invention to provide a *Methylophilus* bacterium, into which the DNA as described above is introduced in an expressible form and has an ability to produce L-lysine or L-arginine.

It is an object of the present invention to provide a method for producing L-lysine or L-arginine, comprising culturing the *Methylophilus* bacterium as described above in a medium and collecting L-lysine or L-arginine from the culture.

It is an object of the present invention to provide the method for producing L-lysine or L-arginine as described above, wherein the medium contains methanol as a main carbon source.

In the present invention, the expression "facilitating excretion of L-lysine, L-arginine or both to the outside of a cell" means that, when a methanol assimilating bacterium containing the DNA of the present invention is cultured in a medium, an increased amount of L-lysine, L-arginine or both is excreted into the medium compared with a methanol assimilating bacterium which does not containing the DNA of the present invention. The promotion of excretion of the L-amino acids from the inside of the cell to the outside of the cell is observed as increased concentrations of the L-amino acids which accumulates in the medium during the culture of the methanol assimilating bacterium containing the DNA of the present invention compared with the concentrations provided by the methanol assimilating bacterium not containing the DNA of the present invention. Furthermore, the promotion of excretion of the L-amino acids to outside of a cell may be also observed as a decrease of the intracellular concentrations of the L-amino acids when the DNA of the present invention is introduced into a methanol assimilating bacterium.

According to the present invention, L-amino acid productivity, especially L-lysine and L-arginine productivity, of a methanol assimilating bacterium is improved.

DESCRIPTION OF THE PREFERRED EMBODIMENTS

Figure 1:
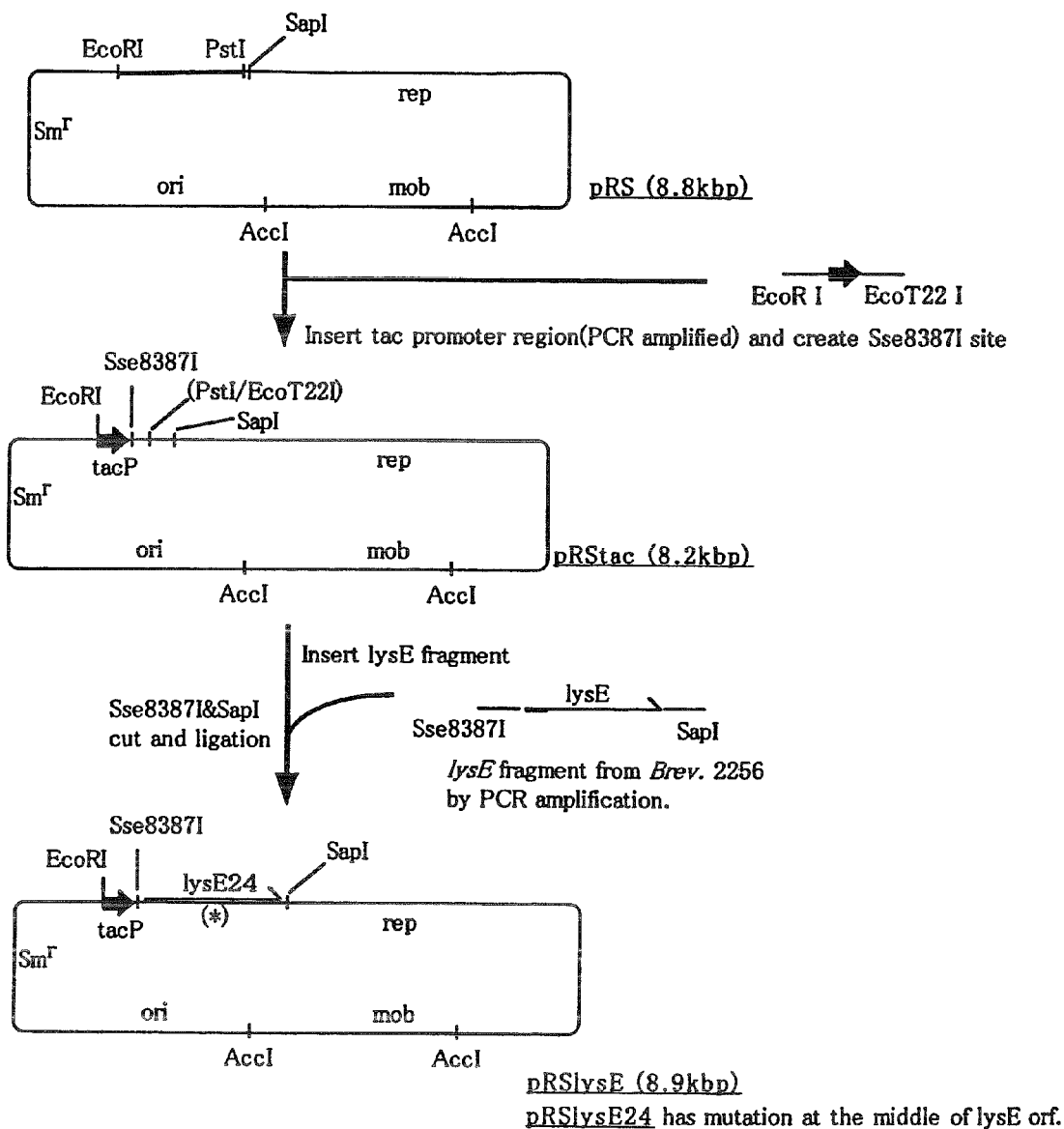
FIG. 1 shows the construction scheme for the plasmid pRStac, which has the tac promoter, and for plasmids pRSlysE and pRSlysE24, which are the plasmid pRStac inserted with either the lysE gene or lysE24 gene, respectively.

Hereafter, the present invention will be explained in detail.
<1>DNA of the Present Invention The DNA of the present invention promotes excretion of L-lysine, L-arginine, or both to the outside of a cell when it is introduced into a methanol assimilating bacterium, and encodes a variant of a protein which is involved in the excretion of L-lysine to the outside of a cell.

In the present invention, the methanol assimilating bacterium can grow by using methanol as the main carbon source. Also secretion of L-amino acids such as L-lysine or L-arginine to the outside of the cell is enhanced by introducing the DNA of the present invention into the methanol assimilating bacterium. Specifically, *Methylophilus* bacteria such as *Methylophilus methylotrophus* can be mentioned. Examples of *Methylophilus methylotrophus* include the AS1 strain (NCIMB10515) and so forth. The *Methylophilus methylotrophus* AS1 strain (NCIMB 10515) can be obtained from the National Collections of Industrial and Marine Bacteria (Address: NCIMB Lts., Torry Research Station 135, Abbey Road, Aberdeen AB98DG, United Kingdom).

The DNA of the present invention can be obtained by introducing a mutation into the DNA which encodes a protein having a loop region and six hydrophobic helixes, and is involved in the secretion of L-lysine to outside of a cell. The mutation results in deletion of the loop region, or deletion of one or more of the hydrophobic helixes. The phrase "deletion of one or more of the hydrophobic helixes" means that the mutant LysE is completely deficient in the loop region or deficient in most of the loop region to such an extent that the function of the mutant LysE is not be affected.

One of the embodiments of the DNA of the present invention is the DNA designated as lysE24, which will be described in the examples mentioned herein. lysE24 is a mutant gene isolated from *Brevibacterium lactofermentum* and is a homologue of the lysE gene which has been reported for *Corynebacterium* bacteria. Therefore, the DNA of the present invention may also be referred to as a "mutant lysE" for convenience.

The LysE protein that is encoded by the lysE gene has six hydrophobic helix regions. Some of these hydrophobic regions are estimated to be transmembrane domains. It is also estimated that the region between the third and fourth regions from the N-terminus is hydrophilic and has a loop structure. In the present invention, this hydrophilic region is called a loop region. The nucleotide sequence of wild-type lysE and the amino acid sequence of the LysE protein of *Brevibacterium lactofermentum* are shown in SEQ ID NOS: 7 and 8. In this amino acid sequence, hydrophobic helix regions correspond to amino acid numbers 5-20, 37-58, 67-93, 146-168, 181-203, and 211-232. The loop region corresponds to amino acid numbers 94-145.

The inventors of the present invention found that the lysE gene exerted lethal action in a methanol assimilating bacterium, but a DNA encoding a variant of the LysE protein that did not have the loop region or substantially consisted only of the hydrophobic helixes promoted the secretion of L-lysine and/or L-arginine to outside of the cell of methanol assimilating bacterium. The DNA of the present invention encodes this mutant LysE protein that does not have the loop region that is present in a wild-type LysE protein, or a mutant LysE protein that substantially consists of only the hydrophobic helixes.

The aforementioned mutant lysE is not particularly limited so long as it has one or more hydrophobic helixes and promotes excretion of L-lysine, L-arginine, or both, when it is introduced into a methanol assimilating bacterium. Specifically, there can be mentioned a DNA encoding a mutant LysE that has all of the first to sixth hydrophobic helixes from the N-terminus. More specifically, there can be mentioned a DNA encoding a peptide containing the first to third hydrophobic helixes from the N-terminus and a peptide containing the fourth to sixth hydrophobic helixes from the N-terminus. The aforementioned lysE24 is an example of the mutant lysE that encodes a peptide containing the first to third hydrophobic helixes, and a peptide containing the fourth to sixth hydrophobic helixes. A mutation is introduced into the lysE24 gene which results in the insertion of a stop codon downstream from the region encoding the third hydrophobic helix. When a region downstream from this stop codon was deleted as described in the examples mentioned later, the *Methylophilus methylotrophus* AS1 strain containing this DNA did not accumulate L-lysine in the medium. From this, it is estimated that a peptide containing the first to third hydrophobic helixes and a peptide containing the fourth to sixth hydrophobic helixes are separately translated and function in *Methylophilus methylotrophus*. In any case, if the lysE24 gene is introduced into a *Methylophilus* bacterium, the production amount of L-lysine or L-arginine is improved.

As the microorganism that is used as an origin of a DNA encoding a protein involved in excretion of L-lysine to outside of a cell, i.e., the lysE gene or its homologous gene, any microorganisms can be utilized so long as it has variants of the genes that can express the L-lysine excretion activity in a methanol-assimilating bacterium. Specifically, there can be mentioned coryneform bacteria such as *Corynebacterium glutamicum* and *Brevibacterium lactofermentum*, *Escherichia* bacteria such as *Escherichia coli*, *Pseudomonas* bacteria such as *Pseudomonas aeruginosa*, *Mycobacterium* bacteria such as *Mycobacterium tuberculosis*, and so forth.

To enhance the amino acid excretion gene in a *Methylophilus* bacterium, a recombinant DNA is prepared by ligating its gene fragment to a vector which is able to function in the *Methylophilus* bacterium, preferably a multi-copy type vector, and introduced into the *Methylophilus* bacterium to transform it. Alternatively, the gene can be incorporated into a transposon and introduced into the chromosome. Furthermore, it is also possible to ligate a promoter that induces strong transcription in a *Methylophilus* bacterium upstream from the gene.

The reference that discloses lysE (WO97/23597) shows only introduction of the lysE gene of coryneform bacterium into a coryneform bacterium. And it mentions only L-lysine as the excreted amino acid, and discloses a protein containing six transmembrane helixes as a novel protein excretion system. However, the inventors of the present invention confirmed that LysE derived from coryneform bacteria did not function at all in methanol assimilating bacteria. Furthermore, the obtained factor is a novel type that exerts the excretion activity. This factor has a basic structure which is different from that of the LysE of coryneform bacteria, and this factor can no way be anticipated from the disclosure of the aforementioned patent specification that discloses lysE having six transmembrane helixes.

<2>*Methylophilus* Bacterium of the Present Invention

The *Methylophilus* bacterium of the present invention is a *Methylophilus* bacterium that is transformed with the DNA of the present invention in an expressible form and has an ability to produce L-lysine or L-arginine. It can be obtained by introducing the DNA of the present invention into a *Methylophilus* bacterium that has the L-lysine or L-arginine producing ability. The *Methylophilus* bacterium of the present invention can also be obtained by imparting an L-lysine or L-arginine producing ability to a *Methylophilus* bacterium which has been transformed with the DNA of the present invention. The *Methylophilus* bacterium of the present invention may also be one that has been imparted with an L-lysine or L-arginine producing ability by introduction of the DNA of the present invention in an expressible form.

A *Methylophilus* bacterium having the L-lysine or L-arginine producing ability can be obtained by imparting an L-lysine or L-arginine producing ability to a wild-type strain of a *Methylophilus* bacterium. In order to impart the L-lysine or L-arginine producing ability, conventionally used methods for breeding coryneform bacteria, *Escherichia* bacteria and so forth, can be used. For example, strains that can be used include auxotrophic mutant strains, analogue resistant strains or metabolic regulation mutant strains, recombinant strains in which an L-lysine or L-arginine biosynthesis system enzyme is enhanced (refer to "Amino Acid Fermentation", the Japan Scientific Societies Press [Gakkai Shuppan Center], 1st Edition, published on May 30, 1986, pp.77 to 100), and so forth. In the breeding of L-lysine or L-arginine producing bacteria, the properties of auxotrophy, analogue resistance, metabolic regulation mutation, and so forth, may be individually imparted, or two or more of them may be imparted in combination. The biosynthesis system enzyme may be individually enhanced or two or more of them may be enhanced in combination. Furthermore, the impartation of these properties may be combined with the enhancement of biosynthesis system enzyme.

For example, L-lysine producing bacteria can be bred so to exhibit auxotrophy for L-homoserine or L-threonine and L-methionine (Japanese Patent Publication Nos. 48-28078 and 56-6499), so to exhibit auxotrophy for inositol or acetic acid (Japanese Patent Laid-open Nos. 55-9784 and 56-8692), or so that they are resistant to oxalysine, lysine hydroxamate, S-(2-aminoethyl)-cysteine, γ-methyllysine, α-chlorocaprolactam, DL-α-amino-ε-caprolactam, α-amino-lauryllactam, aspartic acid analogue, sulfa drug, quinoid, or N-lauroylleucine.

Furthermore, L-arginine producing bacteria can be bred to be resistant to a certain agent, for example, sulfa drug, 2-thiazolealanine, α-amino-β-hydroxyvaleric acid or the like. These bacteria can also be bred so that they exhibit auxotrophy for L-histidine, L-proline, L-threonine, L-isoleucine, L-methionine, or L-tryptophan in addition to being resistant to 2-thiazolealanine (Japanese Patent Laid-open No. 54-44096). They can also be bred so that they are resistant to ketomalonic acid, fluoromalonic acid or monofluoroacetic acid (Japanese Patent Laid-open No. 57-18989), argininol (Japanese Patent Laid-open No. 62-24075), X-guanidine (X represents a derivative of fatty acid or aliphatic chain, Japanese Patent Laid-open No. 2-186995); 5-azauracil, 6-azauracil, 2-thiouracil, 5-fluorouracil, 5-bromouracil, 5-azacytosine, 6-azacytosine and so forth, arginine hydroxamate and 2-thiouracil, arginine hydroxamate and 6-azauracil (refer to Japanese Patent Laid-open No. 57-150381), a histidine analogue or tryptophan analogue (refer to Japanese Patent Laid-open No. 52-114092). These strains can also be bred so that they exhibit auxotrophy for at least one of methionine, histidine, threonine, proline, isoleucine, lysine, adenine, guanine, and uracil (or uracil precursor) (refer to Japanese Patent Laid-open No. 52-99289). They can be bred to be resistant to arginine hydroxamate (refer to Japanese Patent Publication No. 51-6754), exhibit succinic acid auxotrophy or are resistant to a nucleic acid base analogue (Japanese Patent Laid-open No. 58-9692), be deficient in their ability to metabolize arginine and exhibit resistance to an arginine antagonist and canavanine, and exhibit auxotrophy for lysine (refer to Japanese Patent Laid-open No. 52-8729), be resistant to arginine, arginine hydroxamate, homoarginine, D-arginine and canavanine, or resistant to arginine hydroxamate and 6-azauracil (refer to Japanese Patent Laid-open No. 53-143288), be resistant to canavanine (refer to Japanese Patent Laid-open No. 53-3586), and so forth.

Hereinafter, methods for imparting or enhancing L-amino acid producing ability by enhancing an L-amino acid biosynthetic enzyme gene will be exemplified below.

L-lysine producing ability can be imparted by, for example, enhancing activities of dihydrodipicolinate synthase and aspartokinase.

Activities of dihydrodipicolinate synthase and aspartokinase in a *Methylophilus* bacterium can be enhanced by transforming the *Methylophilus* bacterium host with a recombinant DNA prepared by ligating a gene fragment encoding dihydrodipicolinate synthase and a gene fragment encoding aspartokinase with a vector that functions in the *Methylophilus* bacterium, preferably a multiple copy type vector. As a result of the increase in the copy numbers of the gene encoding dihydrodipicolinate synthase and the gene encoding aspartokinase in cells of the transformant strain, activities of these enzymes are enhanced. Hereinafter, dihydrodipicolinate synthase, aspartokinase and aspartokinase III are also referred to as DDPS, AK and AKIII, respectively.

As the microorganism which provides a gene that encodes DDPS and a gene that encodes AK, any microorganism can be used so long as it can express DDPS activity and AK activity. Such microorganisms may be wild-type strains or mutant strains derived therefrom. Specifically, examples of such microorganisms include *E. coli* (*Escherichia coli*) K-12 strain, *Methylophilus methylotrophus* AS1 strain (NCIMB10515), and so forth. Since nucleotide sequences have been determined for the gene encoding DDPS (dapA, Richaud, F. et al., J. Bacteriol., 297 (1986)) and the gene encoding AKIII (lysC, Cassan, M., Parsot, C., Cohen, G. N. and Patte, J. C., J. Biol. Chem., 261, 1052 (1986)), these genes can be obtained by PCR using primers synthesized based on the nucleotide sequences of these genes and chromosomal DNA of a microorganism such as *E. coli* K-12 as a template. As specific examples, dapA and lysC derived from *E. coli* will be explained below. However, genes used for the present invention are not limited to these.

It is preferred that DDPS and AK used for the present invention do not suffer from feedback inhibition by L-lysine. It is known that wild-type DDPS derived from *E. coli* suffers from feedback inhibition by L-lysine, and that wild-type AKIII derived from *E. coli* suffers from suppression and feedback inhibition by L-lysine. Therefore, the dapA and lysC to be introduced into a *Methylophilus* bacterium preferably encode for DDPS and AKIII which has a mutation that eliminates the feedback inhibition by L-lysine, respectively. Hereinafter, DDPS having a mutation that eliminates the feedback inhibition by L-lysine may also be referred to as "mutant DDPS", and a DNA encoding the mutant DDPS may also be referred to as "mutant dapA, or dapA*". AKIII derived from *E. coli* having a mutation that eliminates the feedback inhibition by L-lysine may also be referred to as "mutant AKIII", and a DNA encoding the mutant AKIII may also be referred to as "mutant lysC".

In the present invention, DDPS and AK are not necessarily required to be mutated. It is known that, for example, non-mutated DDPS derived from *Corynebacterium* bacteria does not suffer from feedback inhibition by L-lysine.

The plasmid used for gene cloning may be any plasmid so long as it can replicate in microorganisms such as *Escherichia* bacteria, and there can be specifically mentioned pBR322, pTWV228, pMW119, pUC19, and so forth.

The vector that functions in *Methylophilus* bacteria is, for example, a plasmid that can autonomously replicate in *Methylophilus* bacteria. Specifically, there can be mentioned RSF1010, which is a broad host spectrum vector, and derivatives thereof, for example, pAYC32 (Chistorerdov, A. Y., Tsygankov, Y. D. Plasmid, 16, 161-167 (1986)), pMFY42 (Gene, 44, 53 (1990)), pRP301, pTB70 (Nature, 287, 396, (1980)), and so forth.

In order to prepare a recombinant DNA by ligating dapA and lysC to a vector that functions in a *Methylophilus* bacteria, the vector is digested with a restriction enzyme that corresponds to the terminus of a DNA fragment containing dapA and lysC. Ligation is usually preformed by using ligase such as T4 DNA ligase. dapA and lysC may be individually incorporated into separate vectors or into the same vector.

As a plasmid containing a mutant dapA encoding a mutant DDPS and mutant lysC encoding a mutant AKIII, a broad host spectrum plasmid RSFD80 is known (WO95/16042). *E. coli* JM109 strain transformed with this plasmid was designated AJ12396, and the strain was deposited at the National Institute of Bioscience and Human-Technology, Agency of Industrial Science and Technology, Ministry of International Trade and Industry (currently, the independent administrative corporation, National Institute of Advanced Industrial Science and Technology, International Patent Organism Depositary) on Oct. 28, 1993 and received an accession number of FERM P-13936. Then, it was converted to an international deposit under the provisions of the Budapest Treaty on Nov. 1, 1994, and received an accession number of FERM BP-4859. RSFD80 can be obtained from the AJ12396 strain by a known method.

In order to introduce a recombinant DNA prepared as described above into a *Methylophilus* bacterium, any method can be used so long as it provides sufficient transformation efficiency. For example, electroporation can be used (Canadian Journal of Microbiology, 43, 197 (1997)).

The DDPS activity and AK activity can also be enhanced by the presence of multiple copies of dapA and lysC on the chromosomal DNA of a *Methylophilus* bacterium. In order to introduce multiple copies of dapA and lysC into the chromosomal DNA of a *Methylophilus* bacterium, homologous recombination can be performed by using a sequence that is present on the chromosomal DNA in multiple copies as a target sequence. As a sequence present on the chromosomal DNA in a multiple copies, a repetitive DNA or an inverted repeat present at the end of a transposable element can be used. Alternatively, as disclosed in Japanese Patent Laid-open No. 2-109985, multiple copies of dapA and/or lysC can be introduced into the chromosomal DNA by incorporating them into a transposon and transferring it. In both of the methods, as a result of increased copy numbers of dapA and lysC in transformant strains, the activities of DDPS and AK should be amplified.

Besides the above-described gene amplification, the DDPS activity and AK activity can be amplified by replacing an expression control sequence such as promoters of dapA and lysC with stronger ones (refer to Japanese Patent Laid-open No. 1-215280). Such strong promoters are known, for example, lac promoter, trp promoter, trc promoter, tac promoter, $P_R$ promoter and $P_L$ promoter of lambda phage, tet promoter, amyE promoter, spac promoter and so forth. Substitution of the native promoter with these promoters enhances expression of dapA and lysC, and thus DDPS activity and AK activity are amplified. Enhancement of the expression control sequences can be combined with the increase of the copy numbers of dapA and lysC.

In order to prepare a recombinant DNA by ligating a gene fragment and a vector, the vector is digested with a restriction enzyme which corresponds to the terminus of the gene fragment. Ligation is usually performed by a ligase such as T4 DNA ligase. Typical, well-known methods for digestion, ligation, and others of DNA, preparation of chromosomal DNA, PCR, preparation of plasmid DNA, transformation, design of oligonucleotides used as primers, and so forth, can be used. Such methods are described in Sambrook, J., Fritsch, E. F., and Maniatis, T., "Molecular Cloning A Laboratory Manual, Second Edition", Cold Spring Harbor Laboratory Press (1989) and so forth.

In addition to the enhancement of DDPS and AK, other enzymes involved in L-lysine biosynthesis may also be enhanced. Such enzymes include diaminopimelate pathway enzymes such as dihydrodipicolinate reductase, diaminopimelate decarboxylase, diaminopimelate dehydrogenase (refer to WO96/40934 for all of the foregoing enzymes), phosphoenolpyruvate carboxylase (Japanese Patent Laid-open No. 60-87788), aspartate aminotransferase (Japanese Patent Publication No. 6-102028), diaminopimelate epimerase, and aspartic acid semialdehyde dehydrogenase, aminoadipate pathway enzymes such as homoaconitate hydratase, and so forth.

Aspartokinase, aspartic acid semialdehyde dehydrogenase, dihydrodipicolinate synthase, dihydrodipicolinate reductase, and diaminopimelate decarboxylase derived from *Methylophilus methylotrophus* will be explained herein.

Furthermore, the microorganisms of the present invention may have decreased activity of an enzyme that catalyzes a reaction which generates a compound other than L-lysine by branching off from the biosynthetic pathway for L-lysine, or may be deficient in such an enzyme. Illustrative examples of such an enzyme include homoserine dehydrogenase (see WO95/23864).

The aforementioned techniques for enhancing activities of enzymes involved in the L-lysine biosynthesis can be similarly used for L-arginine.

L-Arginine producing ability can be improved by enhancing acetylornithine deacetylase activity, N-acetylglutamic acid-γ-semialdehyde dehydrogenase activity, N-acetyl glutamokinase activity, and argininosuccinase activity (Japanese Patent Publication No. 5-23750).

L-Arginine producing ability can also be improved by enhancing activity of glutamate dehydrogenase (EP 1 057 893 A1), argininosuccinate synthase (EP0 999 267 A1), carbamoyl phosphate synthetase (EP1 026 247 A1), or N-acetylglutamate synthase (refer to Japanese Patent Laid-open No. 57-5693), or by disrupting the gene encoding an arginine repressor (argR).

<3>Production of L-lysine or L-arginine

L-Lysine or L-arginine can be produced by culturing a *Methylophilus* bacterium having L-lysine or L-arginine producing ability obtained as described above in a medium to produce and accumulate L-lysine or L-arginine in culture, and collecting the L-lysine or L-arginine from the culture.

The microorganism used for the present invention can be cultured by a method usually used for culture of a methanol assimilating microorganism. The medium used for the present invention may be either a natural or synthetic medium so long as it contains a carbon source, nitrogen source, inorganic ions, and other trace amount organic components as required.

If methanol is used as the main carbon source, L-lysine or L-arginine can be produced at a low cost. When methanol is used as the main carbon source, it can be added to the medium in an amount of about 0.001-30%. As the nitrogen source, ammonium sulfate or the like is used by adding it to the medium. Other than these, small amounts of trace components such as potassium phosphate, sodium phosphate, magnesium sulfate, ferrous sulfate, manganese sulfate, and so forth can be added.

The culture is performed under aerobic conditions with shaking, aeration by stirring, or the like at a pH of 5-9 and a temperature of 20-45° C., and it is usually terminated within 24-120 hours.

Collection of L-lysine or L-arginine from the culture can be usually attained by a combination of known methods such as those using ion exchange resin, precipitation, and others.

EXAMPLES

Hereafter, the present invention will be explained more specifically with reference to the following non-limiting examples. The reagents used in the following examples were obtained from Wako Pure Chemicals or Nakarai Tesque unless otherwise indicated. The compositions of the media used in each example are shown below. pH was adjusted with NaOH or HCl for all of the media.

| LB medium: | |
| --- | --- |
| Trypton peptone (Difco) | 10 g/L |
| Yeast extract (Difco) | 5 g/L |
| NaCl | 10 g/L |
| pH 7.0 | |

These were steam-sterilized at 120° C. for 20 minutes.
LB agar medium:
LB medium
Bacto agar 15 g/L
These were steam-sterilized at 120° C. for 20 minutes.

| SEII medium: | |
| --- | --- |
| $K_2HPO_4$ | 1.9 g/L |
| $NaH_2PO_4$ | 1.56 g/L |
| $MgSO_4 \cdot 7H_2O$ | 0.2 g/L |
| $(NH_4)_2SO_4$ | 5 g/L |
| $CuSO_4 \cdot 5H_2O$ | 5 mg/L |
| $MnSO_4 \cdot 5H_2O$ | 25 mg/L |
| $ZnSO_4 \cdot 7H_2O$ | 23 mg/L |
| $CaCl_2 \cdot 2H_2O$ | 0.72 mg/L |
| $FeCl_3 \cdot 6H_2O$ | 9.7 mg/L |
| $CaCO_3$ (Kanto Kagaku) | 30 g/L |
| Methanol | 2% (vol/vol) |
| pH 7.0 | |

Except for methanol, the components were steam-sterilized at 121° C. for 15 minutes.
After the components were sufficiently cooled, methanol was added.

| SEII agar medium: | |
| --- | --- |
| $K_2HPO_4$ | 1.9 g/L |
| $NaH_2PO_4$ | 1.56 g/L |
| $MgSO_4 \cdot 7H_2O$ | 0.2 g/L |
| $(NH_4)_2SO_4$ | 5 g/L |
| $CuSO_4 \cdot 5H_2O$ | 5 mg/L |

-continued

| SEII agar medium: | |
|---|---|
| MnSO$_4$•5H$_2$O | 25 mg/L |
| ZnSO$_4$•7H$_2$O | 23 mg/L |
| CaCl$_2$•2H$_2$O | 0.72 mg/L |
| FeCl$_3$•6H$_2$O | 9.7 mg/L |
| Methanol | 0.5% (vol/vol) |
| pH 7.0 | |
| Bacto agar (Difco) | 15 g/L |

Except for methanol, the components were steam-sterilized at 121° C. for 15 minutes.
After the components were sufficiently cooled, methanol was added.

Example 1

<1>Introduction of lysE Gene Derived from *Brevibacterium* Bacterium into *Methylophilus* Bacterium An lysE gene, which is homologous to the known gene which facilitates the excretion of L-lysine for *Corynebacterium* bacteria, was cloned from a *Brevibacterium* bacterium, and expression in a *Methylophilus* bacterium was attempted.

(1) Construction of pRSlysE

In order to introduce lysE into a *Methylophilus* bacterium, the known plasmid pRS (refer to International Patent Publication in Japanese (Kohyo) No. 3-501682) was used to construct the plasmid pRSlysE, which was used to express lysE. pRS has the vector segment of the pVIC40 plasmid (International Patent Publication WO90/04636, International Patent Publication in Japanese No. 3-501682) and was obtained from pVIC40 by deleting the DNA region encoding the threonine operon in the plasmid. The plasmid pVIC40 is derived from a broad host spectrum vector plasmid pAYC32 (Chistorerdov, A. Y., Tsygankov, Y. D., Plasmid, 1986, 16, 161-167), which is a derivative of RSF1010.

First, plasmid pRStac having the tac promoter was constructed from pRS according to the scheme shown in FIG. 1. The pRStac plasmid was constructed as follows. The pRS vector was digested with the restriction enzymes EcoRI and PstI and a phenol/chloroform solution was added and mixed to terminate the reaction. After the reaction mixture was centrifuged, the upper layer was collected, and DNAs were collected by ethanol precipitation and separated on a 0.8% agarose gel. A DNA fragment of 8 kilobase pairs (henceforth abbreviated as "kbp") was collected by using EASY TRAP Ver. 2 (DNA collection kit, Takara Shuzo). On the other hand, the tac promoter region was amplified by PCR using the pKK223-3 plasmid (expression vector, Pharmacia) as a template and the primers shown in SEQ ID NOS: 1 and 2 (a cycle of denaturation at 94° C. for 20 seconds, annealing at 55° C. for 30 seconds, and extension at 72° C. for 60 seconds was repeated for 30 cycles). Pyrobest DNA polymerase (Takara Shuzo) was used for PCR. The DNA fragment containing the amplified tac promoter was purified by using PCR prep (Promega), and then digested at the restriction enzyme sites preliminarily designed in the primers, i.e., at EcoRI and EcoT22I sites. Then, a phenol/chloroform solution was added to the reaction mixture and mixed to terminate the reaction. After the reaction mixture was centrifuged, the upper layer was collected and DNAs were collected by ethanol precipitation and separated on a 0.8% agarose gel. A DNA fragment of about 0.15 kbp was collected by using EASY TRAP Ver. 2.

The digestion product of the pRS vector and the tac promoter region fragment prepared as described above were ligated by using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies which appeared on the agar medium were each inoculated into LB liquid medium containing 20 mg/L of streptomycin and cultured at 37° C. for 8 hours with shaking. Plasmid DNA was extracted from each culture broth by the alkali-SDS method and the structure of each plasmid was confirmed by digestion with restriction enzymes to obtain pRStac. A plasmid in which the directions of transcription for the streptomycin resistance gene on the pRS vector and the tac promoter were identical was selected as pRStac.

pRStac obtained as described above was digested with Sse8387I (Takara Shuzo) and SapI (New England Biolabs), mixed with a phenol/chloroform solution to terminate the reaction. After the reaction mixture was centrifuged, the upper layer was collected and DNAs were collected by ethanol precipitation and separated on a 0.8% agarose gel to obtain a DNA fragment of about 9.0 kbp.

The lysE gene fragment was also amplified by PCR using the chromosome extracted from the *Brevibacterium lactofermentum* 2256 strain (ATCC13869) as a template and the primers shown in SEQ ID NOS: 5 and 6 (denaturation at 94° C. for 20 seconds, annealing at 55° C. for 30 seconds and extension at 72° C. for 90 seconds). Pyrobest DNA polymerase (Takara Shuzo) was used for PCR. At this time, and so that expression of the lysE gene is possible in a *Methylophilus* bacterium, the primers were designed so that nucleotides of 9-15 bp from the translation initiation codon of the lysE gene were replaced with a sequence that is known to function in a *Methylophilus* bacterium (Wyborn, N. R., Mills, J., Williams, S. G. and Jones, C. W., Eur. J. Biochem., 240, 314-322 (1996)). The obtained fragment was purified by using PCR prep (Promega) and then digested with Sse8387I and SapI. A phenol/chloroform solution was added to the reaction mixture and mixed to terminate the reaction. After the reaction mixture was centrifuged, the upper layer was collected and DNAs were collected by ethanol precipitation and further collected from a 0.8% agarose gel.

The digestion product of the pRStac vector and the lysE gene region fragment prepared as described above were ligated by using DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies which appeared on the agar medium were each inoculated into LB liquid medium containing 20 mg/L of streptomycin and cultured at 37° C. for 8 hours with shaking. Plasmid DNA was extracted from each culture broth by the alkali-SDS method and the structure of each plasmid was confirmed by digestion with restriction enzymes and determination of the nucleotide sequence to obtain pRSlysE (FIG. 1). In pRSlysE, the lysE gene was positioned so that its transcription direction is the same as that of the tac promoter.

(2) Introduction of pRSlysE into *Methylophilus* Bacterium pRSlysE obtained as described above was introduced into *Methylophilus methylotrophus* AS1 strain (NCIMB10515) by electroporation (Canadian Journal of Microbiology, 43, 197 (1997)). In addition, pRS was also introduced into the AS1 strain as a control in the same manner as that for pRSlysE. As a result, several thousands of colonies were obtained per 1 µg of DNA with pRS used as a control, whereas only several colonies were obtained with pRSlysE.

When plasmids were extracted from transformant strains thought to contain pRSlysE, and their nucleotide sequences were investigated, a spontaneous mutation was introduced into a region encoding lysE for all the investigated plasmids, and in some cases, a nonsense mutation was introduced as the mutation, by which a codon encoding an amino acid was replaced with a stop codon that terminated the translation. In other plasmids, a deletion was observed in the lysE gene. It was considered that, in either case, the function of lysE carried by such plasmids should be lost. Furthermore, when a plasmid in which a part of the region encoding lysE was intentionally deleted in such a manner that the function of the lysE gene should be eliminated (pRSlysEΔ1) was prepared, and it was attempted to introduce it into *Methylophilus methylotrophus*, it could be introduced at a frequency equivalent to that of the pRS vector which was used as a control.

The aforementioned pRSlysEΔ1 is a plasmid in which a region from the PvuI site (recognizes CGATCG of the 203-209th positions in SEQ ID NO: 7) to the MluI site (recognizes ACGCGT of the 485-491st positions of the same) in the region encoding lysE is deleted, and it was constructed as follows. Specifically, pRSlysE was digested with PvuI and MluI (Takara Shuzo), a phenol/chloroform solution was added and mixed to terminate the reaction. After the reaction mixture was centrifuged, the upper layer was collected and DNAs were collected by ethanol precipitation and separated on a 0.8% agarose gel to obtain a DNA fragment of about 10 kbp. This DNA fragment was blunt-ended by using DNA Blunting Kit (Takara Shuzo). The product was ligated to itself (self-ligation) by using DNA Ligation Kit Ver. 2 (Takara Shuzo).

This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies which appeared on the agar medium were each inoculated into LB liquid medium containing 20 mg/L of streptomycin and cultured at 37° C. for 8 hours with shaking. Plasmid DNA was extracted from each culture broth by the alkali-SDS method, and the structure of each plasmid was confirmed by digestion with restriction enzymes to obtain the pRSlysEΔ1 plasmid.

As described above, the introduction frequency of pRSlysE carrying the full length lysE gene into *Methylophilus methylotrophus* was extremely low, and only plasmids having an lysE mutant gene containing a mutation that eliminated the function could be introduced. Considering these facts in combination, it was thought that the introduction of the lysE gene into *Methylophilus methylotrophus* resulted in a lethal effect. This indicates that the lysE gene cannot universally function to excrete L-lysine in heterogeneous bacteria.

The *Methylophilus methylotrophus* AS1 strain harboring pRSlysE containing a mutation was applied to an SEII plate containing 20 mg/L of streptomycin and cultured overnight at 37° C. Then, the cells from about 0.3 cm² of the medium surface were scraped, inoculated into SEII production medium (20 ml) containing 20 mg/L of streptomycin, and cultured at 37° C. for 34 hours with shaking. After completion of the culture, the cells were removed by centrifugation and the L-lysine concentration in the culture supernatant was determined by using an amino acid analyzer (Nihon Bunko, high speed liquid chromatography). As a result, substantially no strain was obtained in which excretion of L-lysine was enhanced in spite of introduction of the mutant lysE gene.

<2>Acquisition of Gene Providing L-lysine Excretion Activity in *Methylophilus* Bacteria As described in the preceding section, it was suggested that the known lysE gene should provide a lethal effect in *Methylophilus* bacteria, and many mutant genes with no ability to function were obtained.

During analysis of pRSlysE containing a mutation, a mutant lysE gene that functioned in *Methylophilus* bacteria was obtained.

This mutant lysE gene was designated as the lysE24 gene. When the nucleotide sequence of lysE24 gene was analyzed, it was found that this mutation was not an amino acid substitution, but a nonsense mutation which introduced a stop codon around the middle of the translation region of lysE. It has been reported that the lysE gene of *Corynebacterium* bacteria encodes a membrane protein having six hydrophobic helixes (Vrlijc M., Sahm H., and Eggeling L., Molecular Microbiology 22:815-826 (1996)). In contrast, it was found that, since the above lysE24 gene was introduced with a stop codon, the protein encoded by this gene had a structure different from that of the LysE protein encoded by a wild-type lysE gene, and it functioned in *Methylophilus* bacteria due to this structure.

The result of nucleotide sequence determination of lysE24 is shown in SEQ ID NO: 9. The nucleotide sequence of wild-type lysE is shown in SEQ ID NO: 7 as a reference. In lysE24, T (thymine) was inserted after G (guanine) at the 355th position of SEQ ID NO: 7. The plasmid having this lysE24 was designated as pRSlysE24 (FIG. 1). When pRSlysE24 was introduced anew into the AS1 strain, the plasmid could be introduced at a frequency substantially equivalent to that of pRS. In Table 1, the L-lysine concentration measurement for the culture supernatant of the plasmid-introduced strain is shown, which measurement was performed in the same manner as in <1>, (2).

TABLE 1

| Strain | Production amount of L-lysine (g/L) |
|---|---|
| AS1/pRS | <0.01 |
| AS1/PRSlysE24 | 0.1 |

The *E. coli* JM109 strain transformed with pRSlysE24 was designated as AJ13830, and this strain was deposited at the independent administrative corporation, National Institute of Advanced Industrial Science and Technology, International Patent Organism Depositary on Jun. 4, 2001 and received an accession number of FERM P-18369. Then, it was converted to an international deposition under the provisions of the Budapest Treaty on May 13, 2002, and received an accession number of FERM BP-8040.

When the region downstream from the stop codon produced by the aforementioned mutation in the lysE24 gene was deleted and introduced into the AS1 strain, the strain did not cause accumulation of L-lysine in the medium.

Example 2

Introduction of a Gene Encoding an L-lysine Biosynthesis Enzyme and the lysE24 Gene into *Methylophilus methylotrophus*

It was found that when the lysE24 gene was introduced into *Methylophilus methylotrophus* AS1 strain, L-lysine accumulated in the medium. It was thought that this was caused by the enhancement of the excretion of L-lysine.

The inventors of the present invention had previously clarified that if an L-lysine biosynthesis gene was enhanced by a plasmid in a *Methylophilus* bacterium, a marked amount of L-lysine accumulates in the medium (Japanese Patent Application No. 11-368097). Therefore, the effect of introducing the lysE24 gene into *Methylophilus methylotrophus* which has an L-lysine biosynthesis gene enhanced was investigated.

<1>Construction of the Plasmid pRSdapA Having the dapA* Gene

A plasmid was prepared which has a gene encoding dihydrodipicolinate synthase that did not suffer feedback inhibition by L-lysine (dapA*), as an L-lysine biosynthesis system enzyme gene.

pRStac prepared in Example 1 was digested with Sse8387I and XbaI and a phenol/chloroform solution was added and mixed to terminate the reaction. After the reaction mixture was centrifuged, the upper layer was collected, and DNAs were collected by ethanol precipitation and separated on a 0.8% agarose gel to collect a DNA fragment of about 9 kbp.

The dapA* gene fragment was amplified by PCR using the known plasmid RSFD80 (refer to WO95/16042) containing that gene as a template and the primers shown in SEQ ID NOS: 3 and 4 (denaturation at 94° C. for 20 seconds, annealing at 55° C. for 30 seconds, and extension at 72° C. for 60 seconds). Pyrobest DNA polymerase (Takara Shuzo) was used for PCR. The obtained dapA* fragment was purified by using PCR prep (Promega) and then digested with restriction enzymes Sse8387I and XbaI. A phenol/chloroform solution was added to the reaction mixture mixed to terminate the reaction. After the reaction mixture was centrifuged, the upper layer was collected and DNAs were collected by ethanol precipitation and separated on a 0.8% agarose gel to collect a DNA fragment of about 0.1 kbp.

The digestion product of the pRStac vector and the dapA* gene region fragment prepared as described above were ligated by using the DNA Ligation Kit Ver. 2 (Takara Shuzo). This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies which appeared on the agar medium were each inoculated into LB liquid medium containing 20 mg/L of streptomycin and cultured at 37° C. for 8 hours with shaking. Plasmid DNA was extracted from each culture broth by the alkali-SDS method and the structure of each plasmid was confirmed by digestion with restriction enzymes and determination of the nucleotide sequence to obtain a pRSdapA plasmid. In pRSdapA plasmid, the dapA* gene was positioned so that the direction of transcription was the same as that of the tac promoter.

<2>Introduction of pRSlysE24 or pRSdapA into *Methylophilus methylotrophus* AS1 Strain pRSdapA obtained as described above was introduced into *Methylophilus methylotrophus* AS1 strain by electroporation. As for the obtained transformant (henceforth also referred to as "AS1/pRSdapA"), the aforementioned *Methylophilus methylotrophus* AS1 strain containing the pRSlysE24 (henceforth also referred to as "AS1/pRSlysE24") and the *Methylophilus methylotrophus* AS1 strain containing the pRS plasmid (henceforth also referred to as "AS1/pRS") as a control, the intracellular L-amino acid concentration and the L-amino acid concentration in the culture supernatant were determined.

Each transformant strain was cultured overnight at 37° C. on an SEII plate containing 20 mg/L of streptomycin. Then, the cells from about 0.3 cm² of the medium surface were scraped, inoculated into SEII production medium (20 ml) containing 20 mg/L of streptomycin, and cultured at 37° C. for 24 hours with shaking. After completion of the culture, the cells were removed from a part of the culture broth by centrifugation and the L-amino acid concentration in the culture supernatant was determined by using an amino acid analyzer. The remaining culture broth was passed through silicone oil to separate the culture broth and the cells according to the method of Kinnbier et al. (Dinnbier et al., Arch. Microbiol 150:348-357 (1988)). Amino acids in the cells were extracted with perchloric acid, and the L-amino acid concentration was measured by using an amino acid analyzer. At this time, the protein concentration in the cells was simultaneously measured, and the intracellular L-lysine concentration was represented as an amount per unit weight of the intracellular proteins.

The results are shown in Table 2. With AS1/pRSlysE24, L-lysine accumulation substantially equivalent to that of AS1/pRSdapA was observed in the medium. On the other hand, with AS1/pRSlysE24, the intracellular L-lysine concentration was suppressed to a low level, and it was considered that L-lysine was excreted to outside of the cells due to the introduction of the lysE24 gene.

TABLE 2

| strain | L-lysine concentration in culture supernatant (g/L) | intracellular L-lysine concentration (g/mg-protein) |
|---|---|---|
| AS1/pRS | <0.01 | 1.60 |
| AS1/PRSlysE24 | 0.10 | 2.80 |
| AS1/PRSdapA | 0.12 | 17.3 |

Further, concentrations of other L-amino acids in the culture supernatant were also investigated. As a result, it was found that L-arginine accumulated in AS1/pRSlysE24. Thus, it was found that lysE24 had excretion activity not only for L-lysine but also for L-arginine. The results are shown in Table 3.

TABLE 3

| Strain | L-Arginine concentration in culture supernatant (g/L) |
|---|---|
| AS1/pRS | <0.01 |
| AS1/PRSlysE24 | 0.04 |

The *E. Coli* JM109 strain transformed with the pRSdapA plasmid was designated as AJ13831, and this strain was deposited at the independent administrative corporation, National Institute of Advanced Industrial Science and Technology, International Patent Organism Depositary on Jun. 4, 2001 and received an accession number of FERM P-18370. Then, it was converted to an international deposition under the provisions of the Budapest Treaty on May 13, 2002, and received an accession number of FERM BP-8041.

<3>Introduction of lysE24 Gene and dapA* Gene Into *Methylophilus methylotrophus* AS1 Strain It was found that, although the excretion of L-lysine to the outside of cells constituted a rate-limiting factor in the L-lysine production by *Methylophilus methylotrophus* AS1 strain, the excretion of L-lysine to the outside of cells was enhanced by the introduction of the lysE24 gene. Therefore, it was attempted to further improve the productivity by enhancing the L-lysine biosynthesis enzyme system in a strain introduced with the lysE24 gene.

(1) Construction of Plasmid Having lysE24 and dapA*

Figure 2:
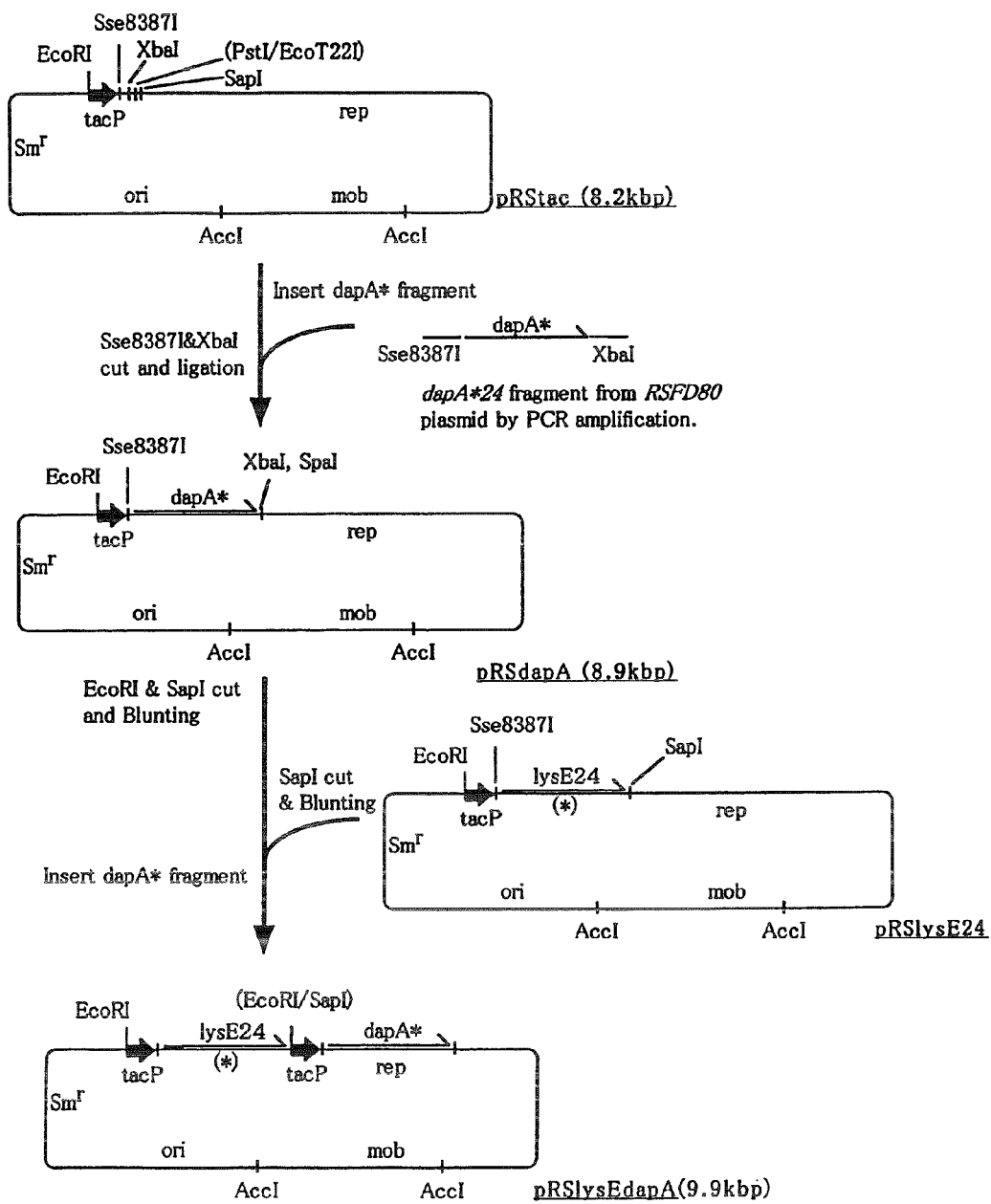
FIG. 2 shows the construction of the plasmid pRSlysEdapA, which has the lysE24 gene and dapA* gene.

In order to evaluate the effect of combining lysE24 and dapA*, a plasmid consisting of the pRSlysE plasmid containing the dapA* gene was constructed in the scheme shown in FIG. 2. pRSlysE24 prepared in Example 1 was digested with a restriction enzyme SapI and ends of the product were blunt-ended by using DNA Blunting Kit (Takara Shuzo). Furthermore, the plasmid pRSdapA having dapA* was digested with restriction enzymes EcoRI and SapI, and a fragment of about 1 kbp containing the tac promoter and the dapA* region was separated on 0.8% agarose gel and collected by using EASY TRAP Ver 2 (Takara Shuzo). This fragment was blunt-ended in the same manner as described above and ligated to the aforementioned digestion product of pRSlysE24 by using DNA Ligation Kit Ver 2 (Takara Shuzo).

This ligation reaction solution was used to transform *Escherichia coli* (*E. coli* JM109 competent cells, Takara Shuzo). The cells were plated on LB agar medium containing 20 mg/L of streptomycin and incubated overnight at 37° C. The colonies appeared on the agar medium were each inoculated into LB liquid medium containing 20 mg/L of streptomycin and cultured at 37° C. for 8 hours with shaking. Plasmid DNA was extracted from each culture broth by the alkali-SDS method, and the structure of each plasmid was confirmed by digestion with restriction enzymes and determination of the nucleotide sequence to obtain a pRSlysEdapA plasmid. In this plasmid, the lysE24 gene and the dapA* gene were positioned so that their transcription directions are identical to each other.

pRSlysEdapA obtained as described above as well as pRSlysE24, pRSdapA and pRS plasmids as controls were each introduced into *Methylophilus methylotrophus* AS1 strain (NCIMB10515) by electroporation.

(2) Production of L-lysine by *Methylophilus* Bacterium Harboring lysE24 and dapA*

Each of the AS1 strains introduced with pRSlysEdapA, pRSlysE24, pRSdapA, or pRS, which were obtained as described above, was applied to an SEII plate containing 20 mg/L of streptomycin and cultured overnight at 37° C. Then, the cells from about 0.3 cm² of the medium surface were scraped, inoculated into SEII production medium (20 ml) containing 20 mg/L of streptomycin, and cultured at 37° C. for 34 hours with shaking. After completion of the culture, the cells were removed by centrifugation and the L-lysine concentration in the culture supernatant was determined by using an amino acid analyzer (Nihon Bunko, high speed liquid chromatography). The results are shown in Table 4. The strain containing the pRSlysEdapA showed L-lysine accumulation in the medium about 10 times higher than that shown by the strain introduced only with pRSdapA or pRSlysE24. Thus, it can be seen that the rate-limiting effect by the excretion was canceled by the introduction of the lysE24 gene and the effect of the enhancement of the dapA* gene was synergistically manifested.

TABLE 4

| Strain | L-Lysine production amount (g/L) |
|---|---|
| AS1/pRS | <0.01 |
| AS1/pRSlysE24 | 0.10 |
| AS1/pRSdapA | 0.12 |
| AS1/pRSlysEdapA | 1.20 |

The *E. coli* JM109 strain transformed with the pRSlysEdapA plasmid was designated as AJ13832, and this strain was deposited at the independent administrative corporation, National Institute of Advanced Industrial Science and Technology, International Patent Organism Depositary on Jun. 4, 2001 and received an accession number of FERM P-18371. Then, it was converted to an international deposition under the provisions of the Budapest Treaty on May 13, 2002, 2002, and received an accession number of FERM BP-8042.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

---

What is claimed is:

1. A method for producing L-lysine or L-arginine comprising
    A) culturing a *Methylophilus* bacterium containing a lysE24 DNA, wherein said lysE24 DNA has been integrated into the chromosome of the bacterium,
    B) allowing L-lysine or L-arginine to be secreted out of said bacterium into said medium, and
    C) collecting the L-lysine or L-arginine.

2. The method for producing L-lysine or L-arginine according to claim 1, wherein said medium contains methanol as the main carbon source.

3. A method for producing L-lysine or L-arginine comprising
    A) culturing a *Methylophilus* bacterium which has been transformed with a plasmid containing a lysE24 DNA in a medium,
    B) allowing L-lysine or L-arginine to be secreted out of said bacterium into said medium, and
    C) collecting the L-lysine or L-arginine.

4. The method for producing L-lysine or L-arginine according to claim 3, wherein said medium contains methanol as the main carbon source.

* * * * *